(12) United States Patent
Sato et al.

(10) Patent No.: US 9,479,135 B2
(45) Date of Patent: Oct. 25, 2016

(54) METHOD FOR MANUFACTURING PIEZOELECTRIC VIBRATION DEVICE

(75) Inventors: Takeo Sato, Imizu (JP); Yuichiro Nagamine, Toyama (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 886 days.

(21) Appl. No.: 13/418,669

(22) Filed: Mar. 13, 2012

(65) Prior Publication Data
US 2012/0174360 A1 Jul. 12, 2012

Related U.S. Application Data

(63) Continuation of application No. PCT/JP2010/052060, filed on Feb. 12, 2010.

(30) Foreign Application Priority Data

Sep. 14, 2009 (JP) .................... 2009-211884

(51) Int. Cl.
*H03H 3/04* (2006.01)
*H03H 9/10* (2006.01)
(Continued)

(52) U.S. Cl.
CPC ............. *H03H 3/04* (2013.01); *C04B 35/46* (2013.01); *C04B 35/48* (2013.01); *H01L 41/22* (2013.01); *H01L 41/25* (2013.01); *H03H 3/02* (2013.01); *H03H 9/10* (2013.01); *H03H 9/105* (2013.01); *H03H 9/1021* (2013.01); *H03H 9/1092* (2013.01); *G01H 3/00* (2013.01); *G01N 29/022* (2013.01); *G01N 29/036* (2013.01); *G01N 2291/0256* (2013.01);
(Continued)

(58) Field of Classification Search
CPC .......... H03H 3/02; H03H 3/022; H03H 3/04; H03H 2003/0485; H03H 9/10; H03H 9/1021; H03H 9/105; H03H 9/1092; C04B 35/46; C04B 35/48; Y10T 29/42; Y10T 29/49005; G01N 29/022; G01N 29/036; G01N 2291/0256; G01N 2291/0426; G01H 13/00; H01L 41/22; H01L 41/25
See application file for complete search history.

(56) References Cited

U.S. PATENT DOCUMENTS 3,652,412 A * 3/1972 Nishida et al. ......... C04B 35/48
5,745,012 A 4/1998 Oka et al.
(Continued)

FOREIGN PATENT DOCUMENTS

CN 1135680 A 11/1996
CN 1381733 A 11/2002
(Continued)

OTHER PUBLICATIONS

PCT/JP2010/05260 Written Opinion dated Jul. 5, 2010.
(Continued)

*Primary Examiner* — A. Dexter Tugbang
(74) *Attorney, Agent, or Firm* — Arent Fox LLP

(57) ABSTRACT

A method for manufacturing a piezoelectric vibration device wherein a substrate is prepared, and a piezoelectric resonator element is mounted on the substrate. Before or after a packaging member is joined to the substrate, the piezoelectric resonator element is exposed to an environment at a higher temperature than ambient temperature and a higher humidity than ambient humidity, and then an electrical property is measured to detect attachment of dust and/or foreign matter according to a variation of the electrical property.

9 Claims, 3 Drawing Sheets

(51) Int. Cl.
*C04B 35/46* (2006.01)
*C04B 35/48* (2006.01)
*H01L 41/22* (2013.01)
*H01L 41/25* (2013.01)
*H03H 3/02* (2006.01)
*G01N 29/02* (2006.01)
*G01N 29/036* (2006.01)
*G01H 3/00* (2006.01)

(52) U.S. Cl.
CPC ............ *G01N 2291/0426* (2013.01); *H03H 2003/022* (2013.01); *H03H 2003/0485* (2013.01); *Y10T 29/42* (2015.01); *Y10T 29/49005* (2015.01)

(56) References Cited

U.S. PATENT DOCUMENTS

| | | | |
|---|---|---|---|
| 5,844,348 A | 12/1998 | Gamo | |
| 6,998,940 B2* | 2/2006 | Metzger | ............ H03H 3/02 |
| 2007/0080611 A1* | 4/2007 | Yamada et al. | .......... H03H 3/02 |
| 2007/0199186 A1* | 8/2007 | Yoshino et al. | .......... H03H 3/02 |
| 2007/0200461 A1 | 8/2007 | Shimodaira | |
| 2008/0078233 A1* | 4/2008 | Larson et al. | ....... G01N 29/036 |

FOREIGN PATENT DOCUMENTS

| | | | |
|---|---|---|---|
| CN | 1415431 A | | 5/2003 |
| CN | 1610247 A | | 4/2005 |
| CN | 1918783 A | | 2/2007 |
| JP | 8-148596 A | | 6/1996 |
| JP | 8-335844 A | | 12/1996 |
| JP | 10-284968 A | | 10/1998 |
| JP | 2008210924 A | * | 9/2008 |
| WO | WO-2009-072351 A1 | | 6/2009 |

OTHER PUBLICATIONS

Chinese Office Action issued for corresponding Application CN 201080040709.4, issue date of Office Action is Dec. 4, 2013 (English translation attached).

* cited by examiner

METHOD FOR MANUFACTURING PIEZOELECTRIC VIBRATION DEVICE

CROSS REFERENCE TO RELATED APPLICATIONS

The present application is a continuation of International application No. PCT/JP2010/052060, filed Feb. 12, 2010, which claims priority to Japanese Patent Application No. 2009-211884, filed Sep. 14, 2009, the entire contents of each of which are incorporated herein by reference.

FIELD OF THE INVENTION

The present invention relates to a method for manufacturing a piezoelectric vibration device, such as a piezoelectric oscillation device, and more specifically, to a method for manufacturing a piezoelectric vibration device including the step of rejecting a defective device caused by attachment of dust or foreign matter.

BACKGROUND OF THE INVENTION

Oscillation devices including a piezoelectric vibration element, such as a quartz vibrator, have been widely used. The piezoelectric oscillation device strongly requires that the oscillation frequency vary little. Accordingly, piezoelectric oscillation devices are measured for resonant frequency, oscillation frequency and other properties after being manufactured, and the piezoelectric oscillation devices having those properties outside permissible ranges are rejected as defectives. Also, if the resonant frequency or oscillation frequency of a measured piezoelectric oscillation device is outside a permissible range, it is attempted to adjust the frequency of the piezoelectric oscillation device.

For example, the below-cited PTL 1 teaches that in manufacture of quartz vibrators, the quartz vibrator is mounted on an insulating substrate and then a small amount of silver is vapor-deposited on the surfaces of electrodes so that the frequency can be adjusted. After adjusting the frequency, in addition, the quartz vibrators are subjected to vacuum lock by vacuum heat baking, followed by ageing, and then the quartz vibrators are screened through the measurement of their electrical properties.

Furthermore, PTL 1 teaches that in such a method, attachment of dust or particles in the manufacturing process is likely to degrade one or more of the properties or to increase the variation of the property. Accordingly, PTL 1 discloses a method for adjusting the frequency by cutting the surface of the electrode of the quartz vibrator chip with plasma.

PTL 1: Japanese Unexamined Patent Application Publication No. 10-284968

SUMMARY OF THE INVENTION

As described in PTL 1, piezoelectric vibration devices, such as piezoelectric oscillation devices, are generally screened by measuring their resonant frequency, oscillation frequency and other properties in the manufacturing process. In this instance, it is common to measure the electrical properties of completed piezoelectric oscillation devices after adjusting the frequency, being subjected to vacuum seal, and then ageing, as disclosed in PTL 1. However, in the process in which electrical properties are measured after ageing at room temperature, it is difficult to reject defectives efficiently in a short time.

For screening based on the properties of electronic components, such as piezoelectric vibration devices, in general, the electronic components are kept at a high temperature and a high humidity, and, then, their electrical properties are measured for the screening. By keeping the electronic components at a high temperature and a high humidity, the degradation of the properties of the electronic components can be accelerated, so that the screening based on properties can be efficiently performed.

However, the method for measuring the properties of electronic components after they are kept at a high temperature and a high humidity accelerates merely the degradation of the properties so as to perform efficient screening based on the properties.

In a piezoelectric oscillation device, such as a quartz vibrator, on the other hand, if the piezoelectric vibration element is contaminated with particles of dust, foreign matter or the like, the properties of the device may be considerably varied during use even if the properties have been within their permissible ranges in the manufacturing process, as suggested in PTL 1. Accordingly, it is desired that the contamination with particles be detected accurately so that products that can turn defective during use can be rejected more highly accurately.

Accordingly, an object of the present invention is to provide a method for manufacturing piezoelectric vibration elements including the step of certainly rejecting potential defectives in the manufacturing stage whose properties can be degraded during use due to attachment of dust, foreign matter or the like, unlike the acceleration test that is performed for merely accelerating the degradation of properties.

According to a broad aspect of the present invention, provided is a method for manufacturing a piezoelectric vibration device, including the steps of: mounting a piezoelectric vibration element on a substrate; and detecting the variation of an electrical property caused by dust or foreign matter absorbing moisture under conditions where the piezoelectric vibration element mounted on the substrate is kept at a higher temperature than ambient temperature and a higher humidity than ambient humidity.

In the step of mounting the piezoelectric vibration element on a substrate, an IC and an electronic component other than the piezoelectric vibration element may further be mounted on the substrate in addition to the piezoelectric vibration element.

According to another broad aspect of the present invention, provided is a method for manufacturing a piezoelectric vibration device including the steps of: mounting a piezoelectric vibration element, an IC, and an electronic component other than the piezoelectric vibration element on a substrate; liquid-tightly sealing the structure in which the piezoelectric vibration element, the IC and the electronic component are mounted on the substrate with a packaging member to obtain the piezoelectric vibration device; keeping the piezoelectric vibration device at a higher temperature than ambient temperature and a higher humidity than ambient humidity; detecting the variation of an electrical property caused by dust and/or foreign matter absorbing moisture while or after the device is kept at a higher temperature than ambient temperature and a higher humidity than ambient humidity.

In this method for manufacturing the piezoelectric vibration device, preferably, the piezoelectric vibration element includes quartz as a piezoelectric vibration body. The piezoelectric material of the piezoelectric vibration element may be a piezoelectric body, such as piezoelectric single crystal or piezoelectric ceramic, other than quartz.

According to another specific aspect of a piezoelectric vibration device of the present invention, the higher temperature than ambient temperature is in the range of 40° C. to 121° C., and the higher humidity than ambient humidity is in the range of 70% RH to 100% RH. Under these conditions, the variation of an electrical property caused by dust or foreign matter absorbing moisture can be reliably and rapidly detected.

In the present invention, the time period for which the temperature higher than ambient temperature and the humidity higher than ambient humidity are kept is, preferably, in the range of 4 hours to 168 hours. By keeping the device under the above conditions for 4 hours or more, the variation of the electrical property caused by dust or foreign matter absorbing moisture can be accurately measured, but by keeping the device under those conditions for more than 168 hours, the manufacturing time cannot be reduced.

In another specific aspect of the piezoelectric vibration device according to the present invention, the variation of the electrical property refers to the variation in resonant frequency and/or resonant resistance. Thus, the variation of an electrical property can readily be detected by measuring the resonant frequency and/or the resonant resistance of the piezoelectric vibration element after the piezoelectric vibration device has been held in an environment of the above-mentioned high temperature and high humidity.

In the method for manufacturing a piezoelectric vibration device according to the present invention, a piezoelectric vibration element mounted on a substrate or a piezoelectric vibration device in which a piezoelectric vibration element, an IC, and an electronic component are mounted on a substrate with a packaging member to liquid-tightly sealing, is kept at a higher temperature than ambient temperature and a higher humidity than ambient humidity. Accordingly, if dust and/or foreign matter is attached to the piezoelectric vibration element, the dust and/or foreign matter absorbs moisture to affect the electrical properties of the piezoelectric vibration element, such as the resonance characteristics. Therefore, the degradation of properties due to attachment of dust and/or foreign matter can be detected by detecting the variation of electrical properties, such as resonance characteristics. Accordingly, such a piezoelectric vibration device can be reliably rejected in course of manufacturing process.

DETAILED DESCRIPTION OF THE PREFERRED EMBODIMENTS

The present invention will be described in detail below, using specific embodiments with reference to the drawings.

Figure 3:
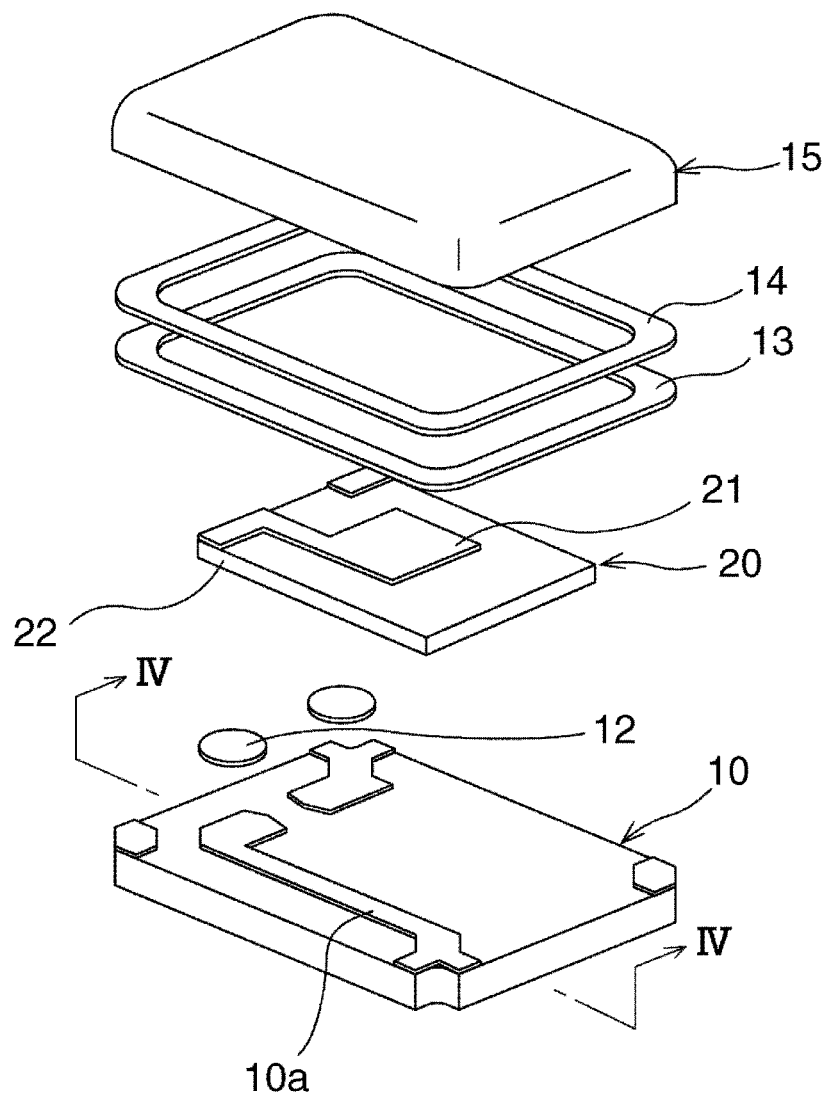
FIG. 3 is an exploded perspective view of a piezoelectric vibration device produced by the method of an embodiment of the present invention.

In a present embodiment, a piezoelectric vibration device used as a piezoelectric oscillator will be produced. The structure of the piezoelectric vibration device is shown in the exploded perspective view of FIG. 3, and in a front sectional view of FIG. 4. The piezoelectric vibration device 1 has a substrate 10. The substrate 10 is made of an insulative material, such as alumina and any other insulating ceramic, or a synthetic resin. Wiring electrodes 10a and 10b are formed on the upper surface of the substrate 10. The wiring electrodes 10a and 10b extend to cutouts formed in the corners of the substrate 10. The wiring electrode portions extending to the cutouts establish external connections. The electrodes 10a and 10b are made of a suitable metal, such as Ag or Cu, or their alloy.

A piezoelectric resonator element 20 as a piezoelectric vibration element is mounted on the substrate 10 with an adhesive 12 therebetween.

The piezoelectric resonator element 20 includes a rectangular piezoelectric plate 22. The piezoelectric plate 22 in the present embodiment is made of quartz. Alternatively, the piezoelectric plate 22 may be made of another piezoelectric single crystal or a piezoelectric ceramic, such as PZT.

The piezoelectric plate 22 is provided with a first resonance electrode 21 on the upper surface thereof. The piezoelectric plate 22 is provided with a second resonance electrode 23 on the lower surface thereof. The first resonance electrode 21 and the second resonance electrode 23 oppose each other with the piezoelectric plate therebetween.

Figure 4:
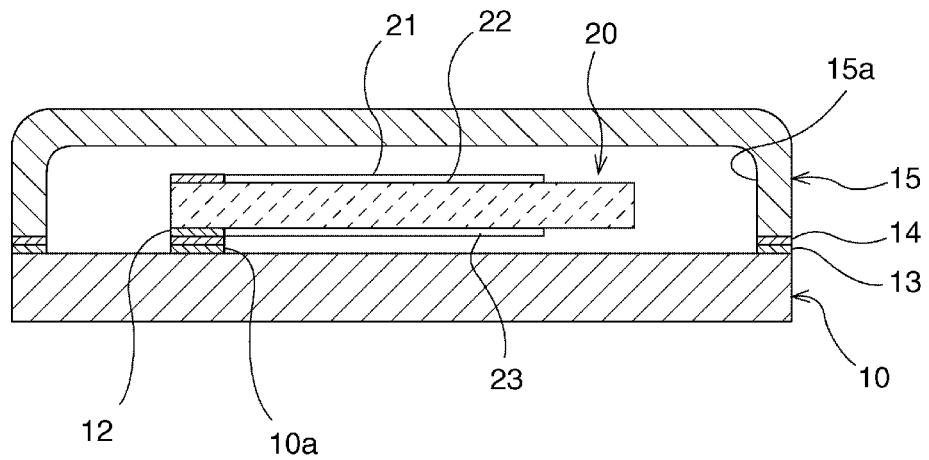
FIG. 4 is a front sectional view of the piezoelectric vibration device produced by the method for manufacturing piezoelectric vibration devices of the embodiment of the present invention.

The first resonance electrode 21 and the second resonance electrode 23 are disposed to one end of the piezoelectric plate 22. The first resonance electrode 21 on the upper surface has an electrode extension extending to the lower surface of the piezoelectric plate 22. The portion of the second resonance electrode 23 reaching the end of the piezoelectric plate 22 is connected to the wiring electrode 10a with the electroconductive adhesive 12, as shown in FIG. 4. The portion of the first resonance electrode extending to the lower surface of the piezoelectric plate 22, not shown in FIG. 4, is also connected to the wiring electrode 10b with the electroconductive adhesive 12 therebetween.

A method for manufacturing the piezoelectric vibration device 1 will now be described with reference to FIG. 1.

Figure 1:
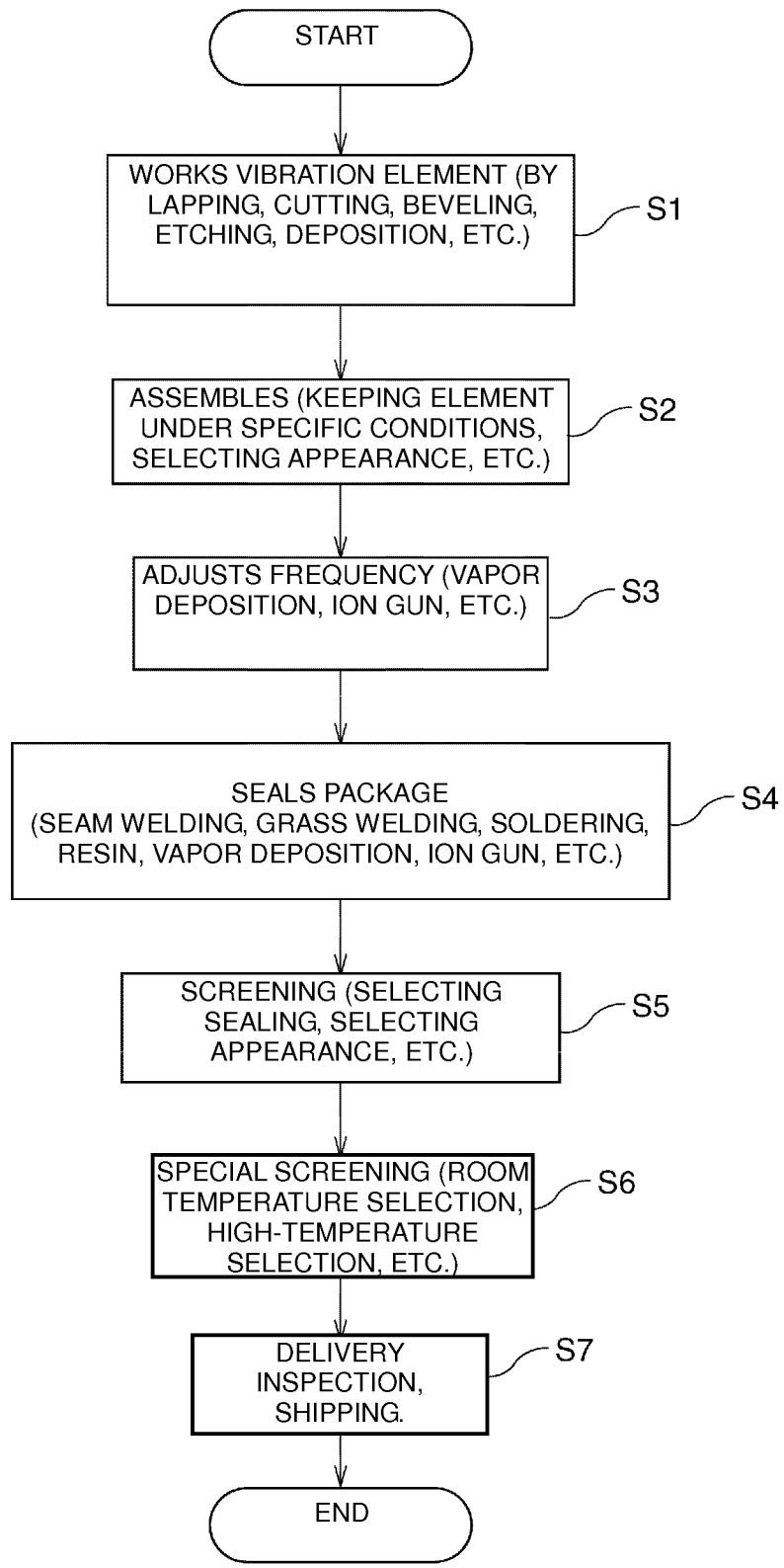
FIG. 1 is a flow diagram illustrating a method for manufacturing piezoelectric vibration devices according to an embodiment of the present invention.

As shown in the flow diagram of FIG. 1, the piezoelectric resonator element 20 is prepared in Step S1. More specifically, the piezoelectric plate 22 may be cut out of a piezoelectric wafer. Alternatively, a piezoelectric wafer may be ground by lapping or the like, or may be formed into the piezoelectric plate 22 by cutting. The piezoelectric plate 22 is provided with the first resonance electrode 21 and the second resonance electrode 23 thereon. Thus the piezoelectric resonator element 20 is prepared in Step S1.

Turning to Step S2, the piezoelectric resonator element 20 is mounted on the substrate 10 with the electroconductive adhesive 12.

Turning to Step S3, the frequency is adjusted. The adjustment of the frequency can be performed by adding a metallic material on the first resonance electrode 21 or the second resonance electrode 23 of the piezoelectric resonator element 20, particularly on the upper resonance electrode 21, by vapor deposition or the like, or using an ion gun, for example. The frequency adjustment method itself can be a known frequency adjustment method as desired.

Then, a packaging member 15 is joined to the substrate 10 in Step S4. More specifically, an adhesive layer 13 and subsequently an insulative material layer 14 are formed in the shape of a rectangular frame, and a metal packaging member 15 is joined to the upper surface of the substrate 10 with the adhesive layer 13 and the insulative material layer 14 therebetween. The insulative material layer 14 is provided for electrically isolating the metal packaging member 15 from the wiring electrodes 10a and 10b on the substrate 10. If the adhesive layer 13 has electric insulation, the insulative material layer 14 may be omitted.

Since the insulative material layer 14 also serves to join the packaging member 15, it is adhesive like the adhesive layer 13. The adhesive layer 13 may be made of, for example, a suitable thermosetting resin, such as epoxy adhesive, or a suitable photo-curable adhesive. The insulative material layer 14 may also be made of a suitable insulating adhesive.

The packaging member 15 has an opening facing downward. The open lower side of the packaging member 15 is joined to the substrate 10 in such a manner that the piezoelectric resonator element 20 is accommodated in the opening. Consequently, the piezoelectric resonator element 20 is enclosed in space A closed by the substrate 10 and the packaging member 15. The adhesive layer 13 and the insulative material layer 14 preferably seals space A in a liquid tight manner. Thus humidity can not enter the sealed space after the space has been formed.

The sealing of space A may be performed by any technique, such as seam welding, glass welding, and soldering, instead of using an adhesive. Thus assembling and sealing of the package are performed in Step S4.

Subsequently, in Step S5, a first screening step is performed for screening based on the seal state of space A, the appearance, or the like. The screening based on the seal state may be performed through, for example, gross leak test or fine leak test. The screening based on the appearance can be performed by visually observing the piezoelectric vibration device 1 directly or through a microscope.

The devices determined to be unwanted in the first screening step are rejected as unwanted products. Subsequently, the piezoelectric vibration devices 1 determined to be conforming products in the first screening step are further screened in a second screening step of Step S6. In the second screening step, an electrical property of the piezoelectric vibration devices 1 is measured at room temperature. In the present embodiment, the resonance characteristic is measured. Thus the resonance characteristic is measured at room temperature. If the measured resonant resistance of a device is outside the permissible range of resonant resistance, the device is rejected as defective.

The feature of the present embodiment is that the second screening step measures the variation of an electrical property resulting from dust or foreign matter absorbing moisture under the conditions where a high temperature and a high humidity are kept for a predetermined time. More specifically, if dust or foreign matter is attached to the piezoelectric resonator element 20, the dust or foreign matter absorbs moisture in the closed space A. Consequently, the resonance characteristics of the piezoelectric resonator element 20 are varied. Since the piezoelectric vibration device 1 is kept under conditions of a high temperature and a high humidity for a predetermined time, moisture largely varies the resonance characteristics. The variation of the resonance characteristics, more specifically, the variation in resonant frequency and resonant resistance, can be obtained from the following equations after measuring the resonance characteristics: variation in resonant frequency $\Delta fr$ (%)={(resonant frequency after being kept at a high temperature and a high humidity−resonant frequency before being kept at a high temperature and a high humidity)/resonant frequency before being kept at a high temperature and a high humidity}×100 (%); and variation in resonant resistance $\Delta CI$={(resistance after being kept at a high temperature and a high humidity−resistance before being kept at a high temperature and a high humidity)/resistance before being kept at a high temperature and a high humidity}×100(%).

When the results of the variation in resonant resistance $\Delta CI$ and the variation in resonant frequency $\Delta fr$ are predetermined values and larger, the device is rejected as defective.

The piezoelectric vibration devices 1 determined to be conforming in the second screening step are finally subjected to delivery inspection in Step S7 and then shipped.

According to the manufacturing method of the present embodiment, piezoelectric vibration devices are subjected to inspection of the seal state and appearance in the first screening step as in the known method for manufacturing piezoelectric vibration devices, and are, in addition, screened to separate conforming devices from defectives according to the variation in resonant resistance and/or the variation in resonant frequency under condition of high temperature and high humidity in the second screening step of Step S6. If a piezoelectric vibration device 1 is kept at a high temperature and a high humidity for a predetermined time, the moisture in the above-described space A is absorbed by dust or foreign matter attached to the piezoelectric resonator element 20 to vary the resonant resistance and/or the resonant frequency much. Therefore, the degradation of properties due to attachment of dust or foreign matter can be accurately detected.

If the piezoelectric resonator element of a piezoelectric vibration device is contaminated with dust or foreign matter, the resonance characteristics of the device may be considerably degraded, so that the initial properties are not shown due to dust or foreign matter absorbing moisture during use, as described above. On the other hand, in the manufacturing method of the present embodiment, degradation in properties due to dust or foreign matter absorbing moisture can be detected in the second screening step. Accordingly, piezoelectric vibration devices 1 that can turn defective during use can certainly be rejected as defective. Thus, highly reliable piezoelectric vibration devices 1 can be shipped.

The step of keeping the devices in an environment of high temperature and high humidity will now be described with reference to specific experimental examples.

Figure 2:
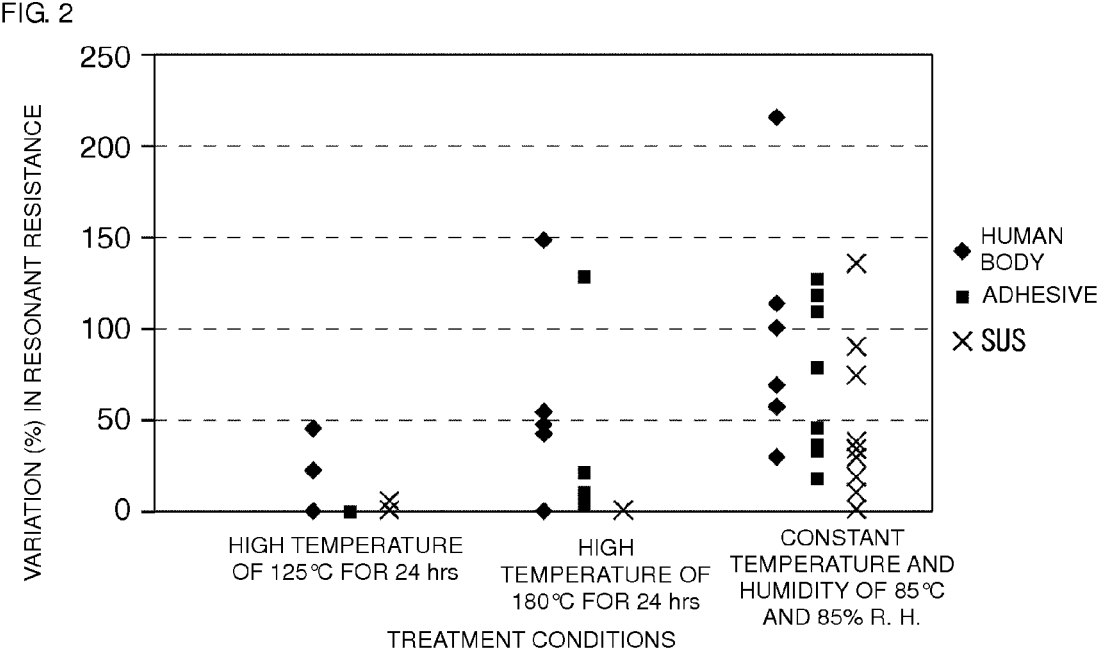
FIG. 2 is a plot showing the variation in resonant resistance of piezoelectric vibration devices placed in environments of 120° C. for 24 hours, of 180° C. for 24 hours, or of 85° C. in temperature and 85% RH in relative humidity in the method of an embodiment of the present invention.

FIG. 2 shows the percentages of variation in resonant resistance when the devices were kept in high-temperature high-humidity environments described in the above embodiment: (1) at a temperature of 125° C. and a relative humidity of 40% RH for 24 hours; (2) at a temperature of 180° C. and a relative humidity of 20% RH for 24 hours; and (3) at a temperature of 85° C. and a relative humidity of 85% RH for 24 hours.

For the measurements, the resonant resistance was measured before keeping the devices in the high-temperature and high-humidity environments, and then, the resonant resistance was measured after keeping the devices in the above environments. The percentage of variation in resonant resistance $\Delta CI$ was thus calculated. Also, the piezoelectric vibration devices 1 whose percentage of variation in resonant resistance had been calculated were divided, and dust or dirt attached to the piezoelectric resonator element 20 was inspected in detail. In FIG. 2, dust derived from the human body, such as skin, is represented by a black rhombus; fine particles of cured adhesive and other fine particles are represented by a black square; and metal powder of stainless steel or others attached in the working step is represented by a cross.

Many piezoelectric vibration devices 1 were subjected to measurement for the percentage of variation in resonant resistance, and were then checked for what type of dust or foreign matter was attached to the devices.

As is clear from FIG. 2, when the devices were merely kept in the environment of (1), that is, at a temperature of 125° C. and a relative humidity of 40% RH, for 24 hours, the variation in resonant resistance was as small as 50% or less for any dust or dirt. Particularly when fragments of cured adhesive or particles of metal powder were attached, the resonant resistance was not varied much. When devices were kept at a temperature of 180° C. and a relative humidity of 20% RH for 24 hours, the variation in resonant resistance became larger than under conditions of (1). Particularly when fragments of cured adhesive were attached, and even when dust derived from the human body was attached, the variation in the environment of (2) was larger than that in the environment of (1). However, attached metal powder or the like did not vary the resonant resistance much. On the other hand, when devices were kept in the environment of (3), that is, at a temperature of 85° C. and a relative humidity of 85% RH, the variation in resonant resistance was significantly large for any case where the piezoelectric vibration device was contaminated with dust derived from the human body, fragments of cured adhesive, or metal powder.

Thus, it has been shown that, by keeping devices in an environment where the relative humidity is as high as 85% RH and is hence higher than in the environments of (1) and (2), the variation in resonant resistance is significantly increased when dust or dirt is attached to the devices.

In the present invention, the contamination with a variety of dust and foreign matter can certainly be detected by measuring the variation in resonant resistance of piezoelectric vibration devices 1 with the devices kept in an environment of not only a high temperature, but also a high humidity in the second screening step.

In the above Experimental Example (3), devices were kept in an environment at a temperature of 85° C. and a relative humidity of 85% RH for 24 hours. Since dust and foreign matter can absorb moisture as long as the temperature is higher than ambient temperature and the humidity is higher than ambient humidity, the contamination with dust or foreign matter can be detected more reliably than in the case where the devices are kept at the same temperature and the same humidity as ambient temperature and ambient humidity, as in the above Experimental Example. In particular, it is important that the devices are kept not only at a high temperature, but also at a higher humidity than ambient humidity, as is clear from the above Experimental Examples.

Preferably, the higher temperature than ambient temperature is in the range of 40° C. to 121° C. Temperatures of less than 40° C. are not different much from room temperature or about 25° C., and temperatures of more than 121° C. may degrade the material of the piezoelectric vibration device 1.

Preferably, the high humidity is in the range of 70% RH to 100% RH in relative humidity. If the humidity is less than 70% RH, the variation of a property of the device resulting from a variety of dust or foreign matter absorbing moisture cannot be increased, as is clear from the above Experimental Examples. In particular, the variation in resonant resistance when metal powder is attached cannot be increased. Also, if the relative humidity is more than 100% RH, condensation occurs in the piezoelectric resonator element 20. This is not preferable.

The time period for which a high temperature and a high humidity are kept is not limited to 24 hours, which was set in the above Experimental Examples. As long as devices are kept for a certain time in the above environment, the variation in resonant resistance can be increased, as is clear from the above Experimental Examples. Preferably, the time period is in the range of 4 to 168 hours. A time period of less than 4 hours may not significantly increase the variation in resonant resistance. A time period of more than 168 hours increases the time for the step of screening based on properties, and, hence, the time of the manufacturing process cannot be reduced.

In the above embodiment, the resonance characteristics are measured, and the variation in resonant resistance and resonant frequency are calculated. However, the variation in anti-resonant resistance may be obtained instead of the variation in resonant resistance, or the variation of frequency itself may be obtained, such as resonant frequency or anti-resonant frequency. Also, the variation of an electrical property other than resonance characteristics may be obtained. In any case, it is suggested that the variation of an electrical property varied by dust or foreign matter absorbing moisture be obtained.

In the manufacturing method of the above embodiment, the variation of a property due to attachment of dust or foreign matter was measured after keeping the device under conditions of a high temperature and a high humidity with the piezoelectric resonator element 20 sealed with the packaging member 15. However, the variation of a property may be measured after keeping the device at a high temperature and a high humidity before the packaging member 15 is joined to the substrate 10. Although in this instance, dust or foreign matter may contaminate space A during the step of joining the packaging member 15 to the substrate 10, or in a subsequent step, defectives due to dust or foreign matter attached before these steps can certainly be rejected.

It is however preferable that the above-described screening be performed after the packaging member 15 has been joined to the substrate 10, as in the above embodiment. The piezoelectric vibration device manufactured in the present embodiment may not have the packaging member 15. In such a case, the variation of an electrical property can be measured after the piezoelectric resonator element 20 mounted on the substrate 10 has been kept under conditions of a high temperature and a high humidity, and then screening based on the property can be performed.

REFERENCE SIGNS LIST 1 piezoelectric vibration device
10 substrate
10a, 10b wiring electrode
12 electroconductive adhesive
13 adhesive layer
14 insulative material layer
15, 16 packaging member
20 piezoelectric resonator element
21 first resonance electrode
22 piezoelectric plate
23 second resonance electrode

The invention claimed is:

1. A method for manufacturing a piezoelectric vibration device, the method comprising:
   mounting a piezoelectric vibration element on a substrate;
   exposing the piezoelectric vibration element to a temperature higher than an ambient temperature and to a humidity higher than an ambient humidity; and
   detecting a variation of an electrical property caused by dust or contaminating foreign matter that is attached to the piezoelectric vibration element and that absorbs moisture while the piezoelectric vibration element is kept at the temperature higher than the ambient temperature and at the humidity higher than the ambient humidity.

2. The method for manufacturing a piezoelectric vibration device according to claim 1, wherein an IC and an electronic component other than the piezoelectric vibration element are further mounted on the substrate.

3. The method for manufacturing a piezoelectric vibration device according to claim 1, wherein the piezoelectric vibration element includes quartz as a piezoelectric vibration body.

4. The method for manufacturing a piezoelectric vibration device according to claim 1, wherein the temperature higher than ambient temperature is in a range of 40° C. to 121° C.

5. The method for manufacturing a piezoelectric vibration device according to claim 4, wherein the humidity higher than ambient humidity is in a range of 70% RH to 100% RH.

6. The method for manufacturing a piezoelectric vibration device according to claim 1, wherein the humidity higher than ambient humidity is in a range of 70% RH to 100% RH.

7. The method for manufacturing a piezoelectric vibration device according to claim 1, wherein a time period for which the temperature higher than ambient temperature and the humidity higher than ambient humidity are kept is in a range of 4 hours to 168 hours.

8. The method for manufacturing a piezoelectric vibration device according to claim 1, wherein the variation of the electrical property is at least one of a variation of resonant frequency and resonant resistance.

9. The method for manufacturing a piezoelectric vibration device according to claim 1, further comprising:
   comparing a value of the variation of the electrical property with a predetermined value; and
   classifying the piezoelectric vibration device as defective if the value of the variation of the electrical property is equal to or greater than the predetermined value.

* * * * *